United States Patent [19]

Meixner et al.

[11] Patent Number: 4,748,269

[45] Date of Patent: May 31, 1988

[54] PROCESS FOR THE PREPARATION OF (METH)ACRYLIC ACID ESTERS AND THEIR USE

[75] Inventors: Jürgen Meixner, Krefeld; Josef Pedain, Cologne; Peter Höhlein, Kempen; Dieter Margotte, Krefeld, all of Fed. Rep. of Germany

[73] Assignee: Bayer Aktiengesellschaft, Leverkusen, Fed. Rep. of Germany

[21] Appl. No.: 851,742

[22] Filed: Apr. 14, 1986

[30] Foreign Application Priority Data

Apr. 20, 1985 [DE] Fed. Rep. of Germany ....... 3514402

[51] Int. Cl.$^4$ ............................................. C07C 69/52
[52] U.S. Cl. .................................... 560/205; 560/218
[58] Field of Search ................................ 560/205, 218

[56] References Cited

U.S. PATENT DOCUMENTS 2,917,538  12/1959  Carlyle ................................ 560/205

FOREIGN PATENT DOCUMENTS 1030459  7/1953  France .
2376117  12/1977  France .

OTHER PUBLICATIONS

Khorana, H. G. *Chemical Reviews*, vol. 53 (1953), pp. 145–166.

*Primary Examiner*—Paul J. Killos
*Attorney, Agent, or Firm*—Sprung Horn Kramer & Woods

[57] ABSTRACT

(Meth)acrylic acid esters can be prepared by acid-catalyzed reaction of (meth)acrylic acid with alcohols in a water-immiscible solvent. After the esterification, the reaction mixture is washed with aqueous solutions having an alkaline reaction and then reacted at elevated temperature with carbodiimides. Acid numbers below 0.5 (mg of KOH/g of substance) are obtained in this way. (Meth)acrylic acid esters are used, for example, as reactive diluents or as comonomers.

10 Claims, No Drawings

PROCESS FOR THE PREPARATION OF (METH)ACRYLIC ACID ESTERS AND THEIR USE

The invention relates to a process for the preparation of (meth)acrylic acid esters of low acid number by esterification of (meth)acrylic acid with monohydric or polyhydric alcohols and subsequent treatment with carbodiimides, and to their use as reactive diluents and as comonomers.

The use of (meth)acrylic acid esters of monohydric or polyhydric alcohols as reactive diluents or comonomers, preferably as reactive diluents in radiation-curable coating compositions, is known in principle. The preparation of such (meth)acrylic acid esters is in general carried out by azeotropic esterification of (meth)acrylic acid with the corresponding alcohols in an inert solvent, using an acid esterification catalyst in the presence of stabilizers. After the esterification has been completed, the catalyst is washed out and the solvent is distilled off.

Even if a neutralisation is carried out in connection with the washing-out of the catalyst, a residual acid number of up to 3 (mg of KOH/g of substance) remains in most cases. The retention of the residual acid number means, however, that the residues of (meth)acrylic acid manifest themselves during handling by an odor, by corrosion of vessels and sometimes skin irritation.

Attempts have been made to solve the problem by adding slaked lime after the preparation of the (meth)acrylic acid ester and removing the resulting insoluble calcium salt by filtration (U.S. Pat. No. 3,717,672). In this case, however, resinous precipitates which are difficult to filter are frequently formed.

Moreover, a process for the preparation of (meth)acrylic acid esters is known, in which, after the neutralization of the esterification catalyst, the residual (meth)acrylic acid is reacted with an epoxide compound (European Pat. No. 127,766). In this case again, however, products with acid numbers greater than 1 (mg of KOH/g of substance) are formed. Depending on the nature and quantity of the epoxide employed, the viscosity of the end product then also changes to different degrees.

It was therefore desirable to prepare (meth)acrylic acid esters in such a way that the end product has a still further reduced acid number, without the properties of the polymerizable mixtures prepared with the end product, such as their color number, viscosity or reactivity, being adversely affected; at the same time, the reaction time for the preparation of the (meth)acrylic acid esters should not be unduly prolonged.

The object was achieved by reacting the residual (meth)acrylic acid after the reaction of the esterification components with a carbodiamide. In this case, a marked improvement, as a reduced acid number, to values below 0.5 (mg of KOH/g of substance), frequently to at most 0.3, is achieved.

Accordingly, the invention relates to a process for the preparation of esters of (meth)acrylic acid by acid-catalyzed reaction of (meth)acrylic acid with alcohols in a water-immiscible solvent, which is characterized in that the reaction mixture is initially washed with aqueous solutions having an alkaline reaction, washed with water until neutral and then reacted at an elevated temperature with carbodiimides.

Both acrylic acid and methacrylic acid and also a mixture of the two can be employed as the acid in the process according to the invention.

The alcohols employed for the process according to the invention can be monohydric or polyhydric, saturated, aliphatic or cycloaliphatic alcohols which optionally contain ether groups. Such alcohols have molecular weights from 32 to about 400. By way of example, the following alcohols may be mentioned: methanol, ethanol, propanols, butanols, hexanols, cetyl alcohol, stearyl alcohol, ethylene glycol, propylene glycol, 1,4-butane diol, 1,5-pentane diol, neopentyl glycol, 1,6-hexane diol, glycerol, trimethylolethane, trimethylolpropane, pentaerythritol, 2-ethylhexanol, cyclohexanol, dimethylolcyclohexane and oxalkylation products of the said alcohols with, for example, 1–5 moles of ethylene oxide or propylene oxide per hydroxyl equivalent. In the case of the use of (meth)acrylic acid esters, prepared according to the invention, as comonomers, the starting material preferably consists of lower alcohols, for example those having 1–6 C atoms, preferably 1–2 C atoms, whereas higher alcohols, for example those having molecular weights of 62 to about 400, are the starting materials for use of the (meth)acrylic acid esters as reactive diluents.

In general, 70–150 mol % of acrylic and/or methacrylic acid, preferably 85–120 mol %, particularly preferably 0.95–1.10 mol %, relative to hydroxyl equivalents present, are employed.

The acid esterification catalysts used can be inorganic or organic acids or acid ion exchangers in a quantity of 0.1–3 % by weight, relative to the weight of the reaction components to be esterified. Examples of such esterification catalysts are sulphuric acid, phosphoric acid, pyrophosphoric acid, p-toluenesulphonic acid, styrene/divinylbenzene-sulphonic acid cation exchangers, chlorosulphonic acid and chloroformic acid, preferably sulphuric acid and p-toluene sulphonic acid.

The process according to the invention is carried in a solvent which is immiscible with water and which can be distilled with water in the manner of a steam distillation. For this purpose, hydrocarbons and their halogen or nitrosubstitution products as well as further solvents, which neither react with reactants nor are changed under the influence of the acid catalysts, can be used. In a preferred manner, unsubstituted hydrocarbons are employed. By way of example, the following may be mentioned: aliphatic hydrocarbons, such as hexane, heptane, octane and gasoline fractions of various boiling ranges, cycloaliphatic hydrocarbons, such as cyclopentane, cyclohexane or methylcyclohexane, or aromatic hydrocarbons, such as benzene, toluene or the isomeric xylenes. In a preferred manner, those solvents are employed which boil in the range of 70°–120° C.. Cyclohexane, toluene or gasoline fractions in the boiling range of 70°–120° C. may be mentioned here in particular. The water-immiscible solvent can also be a mixture of the abovementioned substances. It is employed in a quantity of 10–100% by weight, preferably 15–50% by weight, particularly preferably 20–40% by weight, relative to the weight of the reaction component which is to be esterified.

The process according to the invention can be carried out in the presence of one or more polymerization inhibitors in a quantity of 0.01–1% by weight, preferably 0.1–0.5% by weight, relative to the mixture of (meth)acrylic acid and alcohol, which is to be esterified. Such inhibitors are described, for example, in Houben-Weyl, Methoden der organischen Chemie [Methods of organic chemistry], 4th edition, volume XIV/1, Georg Thieme Verlag, Stuttgart 1961, page 433 et seq. The following may be mentioned as examples: sodium dithionite, sodium hydrogen sulphide, sulphur, hydrazine, phenylhydrazine, hydrazobenzene, N-phenyl- β-naphthylamine, N-phenyl-ethanolamine, dinitrobenzene, picric acid, p-nitroso-dimethylaniline, diphenylnitrosamine, phenols such as p-tert.-butyl-pyrocatechol, 2,5-di-tert.-amyl-hydroquinone, p-alkoxyphenols, di-tert.-butylhydroquinone, tetramethyl thiuram disulphide, 2-mercapto-benzothiazole and sodium dimethyl-dithiocarbamate.

Furthermore, in a preferred variant of the process according to the invention, an oxygen-containing gas, preferably air, is passed into the reaction mixture.

The process according to the invention is carried out initially for the esterification in a temperature range of 60°–140° C., preferably 70°–120° C., particularly preferably at the boiling point of the solvent employed. During this process, solvent is continuously stripped from the reaction mixture by distillation, separated outside the reaction vessel in a water separator from entrained water and then returned again in the reaction mixture. The end of the reaction has been reached when further water of reaction is no longer entrained out of the reaction vessel.

After the end of the esterification, the reaction mixture is washed with an aqueous alkaline solution, such as dilute sodium hydroxide solution, dilute potassium hydroxide solution or an aqueous solution of alkali metal carbonates, alkali metal bicarbonates or ammonia, preferably with dilute aqueous sodium hydroxide solution. Subsequently, the reaction mixture is washed with water until neutral.

The reaction mixture is then reacted with one or more carbodiimide(s) at a temperature of 40°–120° C., preferably 50–100° C., particularly preferably 70°–90° C., until the acid number has fallen to the desired value, for example to a value of <0.5 (mg of KOH/g of substance). For the reaction with carbodiimide, the acidity obtained after the wash described above is determined and carbodiimide(s) is or are then added in a ratio of 1–4 moles per carboxyl group equivalent; a molar ratio of 1.0–2.5 moles of carbodiimide per carboxyl equivalent is preferred.

Examples of carbodiimides which can be employed according to the invention are those with aliphatic, cycloaliphatic, aromatic or aromatic-aliphatic substituents, such as diethylcarbodiimide, dicyclohexylcarbodiimide, diphenylcarbodiimide, dibenzylcarbodiimide, di-(isopropylphenyl)-carbodiimide, di-(methylphenyl)-carbodiimide and polycarbodiimides resulting from the reaction of carbodiimides with diisocyanates. Carbodiimides and polycarbodiimides of the type mentioned are known, for example, from Angew. Chem. 74, 1962, page 801, in particular page 806.

The reaction of the washed esterification mixture with carbodiimide can be carried out in the presence or absence of the water-immiscible solvent. In a preferred manner, the reaction with the carbodiimide is carried out, after the water-immiscible solvent has been distilled off from the reaction mixture which has been washed until neutral, for example under a reduced pressure, about 10–50 mbar, and at an elevated temperature, for example 70°–100° C..

Because of the unpredictable reactions to be expected between the carbodiimide and the (meth)acrylic acid ester, as a result of which undesired changes in viscosity, color number and reactivity might be expected, the smooth and successful procedure of the process according to the invention is surprising.

The (meth)acrylic acid esters obtainable according to the invention are used as reactive diluents or as comonomers in mixtures with other olefinically unsaturated compounds. They are used in particular as reactive diluents in radiation-curable coating compositions. The invention therefore also relates to these uses of the (meth)acrylic acid esters obtainable in the process described.

EXAMPLES

In the examples which follow, the percentage data relate to the weight of the reaction components which are to be esterified. The viscosity measurements were carried out at 20° C. in a Rheometer from Messrs. Contraves. The iodine colour numbers were determined according to DIN 6162.

In the examples, the condensation was carried out at 70% concentration in toluene in the presence of 0.75% of p-toluenesulphonic acid as the catalyst and 0.1% of p-methoxyphenol and 0.1% of di-tert.-butyl-hydroquinone as the inhibitors.

The starting components listed in the table as well as the catalyst and the inhibitors were heated in toluene at 110°–120° C., with passing in air, until water no longer separated out. After cooling to 20°–30° C., the organic phase was washed once with dilute aqueous sodium hydroxide solution and twice with water. The toluene was then distilled off at 80°–90° C. under 50–60 mbar. After measurement of the acid number, the particular carbodiimide (see table) was added and the mixture was kept at 80° C. until the acid number had reached the desired value (about 1 to 4 hours). The mixture was then filtered, and the final characteristic data listed in the table were measured.

TABLE

| | Examples | | |
|---|---|---|---|
| Starting components (parts) | 1 | 2 | 3 |
| Acrylic acid | 191 | 120 | 139 |
| 1,6-Hexanediol | 156 | — | — |
| Tripropylene glycol | — | 169 | 195 |
| Data after condensation | | | |
| Acid number (mg of KOH/g of substance) | 5.0 | 2.4 | 2.4 |
| Viscosity (mPa.s) | 8 | 16 | 16 |
| Color number | 0–1 | 1–2 | 1–2 |
| Addition of (parts) | | | |
| Dicyclohexylcarbodiimide | 5.5 | 2.3 | |
| Diisopropylphenylcarbodiimide | — | — | 7.1 |
| Final data | | | |
| Acid number (mg of KOH/g of substance) | 0.4 | 0.2 | 0.2 |
| Viscosity (mPa.s) | 8 | 16 | 16 |
| Color number | 0–1 | 1–2 | 1–2 |

What is claimed is:

1. A process for reducing the acid number of an ester of (meth)acrylic acid wherein said meth(acrylic) acid ester is prepared by the acid-catalyzed esterification of (meth)acrylic acid with an alcohol in a water-immiscible solvent said process comprising (1) washing the esterification reaction mixture obtained from the reaction of (meth)acrylic acid with an alcohol with an aqueous alkaline solution; (2) washing the aqueous alkaline solution washed esterification reaction mixture with water until neutral to obtain a neutral esterification reaction mixture; and (3) reacting said neutral esterification reaction mixture at an elevated temperature with a carbodiimide.

2. A process according to claim 1, wherein 1.0 to 2.5 moles of carbodiimide are employed per equivalent of residual acid.

3. A process according to claim 1, wherein 1-4 moles of carbodiimide are employed per equivalent of residual acid.

4. A process according to claim 1, wherein the reaction with carbodiimide is carried out at 40°-120° C.

5. A process according to claim 1, wherein the reaction with carbodiimide is carried out at 50°-100° C.

6. A process according to claim 1, wherein the reaction mixture which is to be reacted with carbodiimide was prepared while passing an oxygen-containing gas there through.

7. A process according to claim 1 wherein before the reaction with carbodiimide, the water-immiscible solvent is distilled off from the reaction mixture which has been washed until neutral.

8. A process according to claim 1, wherein the carbodiimide is an aliphatic, cycloaliphatic, aromatic, aromatic-aliphatic carbodiimide.

9. A process according to claim 1, wherein the carbodiimide is a polycarbodiimide.

10. An ester of (meth) acrylic acid prepared by the process according to claim 1 wherein said (meth) acrylic acid ester has an acid number below 0.5.

* * * * *